(12) United States Patent
Bolz

(10) Patent No.: US 12,350,492 B2
(45) Date of Patent: Jul. 8, 2025

(54) DEVICE FOR PERFORMING tVNS TREATMENT

(71) Applicant: tVNS Technologies GmbH, Erlangen (DE)

(72) Inventor: Armin Bolz, Buckenhof (DE)

(73) Assignee: TVNS TECHNOLOGIES GMBH, Erlangen (DE)

( * ) Notice: Subject to any disclaimer, the term of this patent is extended or adjusted under 35 U.S.C. 154(b) by 364 days.

(21) Appl. No.: 16/987,929

(22) Filed: Aug. 7, 2020

(65) Prior Publication Data
US 2021/0038893 A1    Feb. 11, 2021

(30) Foreign Application Priority Data
Aug. 9, 2019   (DE) .................... 10 2019 121 583.8

(51) Int. Cl.
| A61N 1/36 | (2006.01) |
| A61M 21/02 | (2006.01) |
| A61N 1/04 | (2006.01) |
| A61M 21/00 | (2006.01) |

(52) U.S. Cl.
CPC ......... *A61N 1/36034* (2017.08); *A61M 21/02* (2013.01); *A61N 1/0456* (2013.01); *A61M 2021/0027* (2013.01); *A61M 2021/0072* (2013.01)

(58) Field of Classification Search
CPC .. A61N 1/36025; A61N 1/025; A61N 1/0456; A61N 1/36031; A61N 1/36034; A61N 1/36053; A61N 1/36114; A61N 1/36014; A61B 5/08; A61B 5/11; A61B 5/369; A61B 5/4029; A61B 5/0531; A61B 5/4035; A61B 2560/0242; A61B 5/0245; A61B 5/0816; A61B 5/4836
See application file for complete search history.

(56) References Cited

U.S. PATENT DOCUMENTS

| 2015/0142082 A1* | 5/2015 | Simon ................ A61N 1/36132 607/61 |
| 2016/0022206 A1* | 1/2016 | Simon .................. A61B 5/4064 600/301 |
| 2016/0303371 A1* | 10/2016 | Whiting ............... A61B 5/6831 |
| 2017/0021172 A1* | 1/2017 | Perez ................. A61N 1/37211 |

FOREIGN PATENT DOCUMENTS

| DE | 10 2011 100 065 A1 | 10/2012 |
| WO | 2012/139603 A1 | 10/2012 |
| WO | 2018/050773 A1 | 3/2018 |

* cited by examiner

*Primary Examiner* — Amanda K Hulbert
*Assistant Examiner* — Natasha Patel
(74) *Attorney, Agent, or Firm* — McCoy Russell LLP

(57) ABSTRACT

The present invention relates to a device for performing a tVNS treatment having at least one electrode for generating a stimulation pulse, wherein the device has at least one input device for inputting feedback data by the device user, wherein the device has a memory in which the feedback data are stored, and wherein the device has a control or regulation unit that is suitable to set one or more parameters of the stimulation pulse delivered by the electrode in dependence on the feedback data or to suggest the parameters of the stimulation pulse delivered by the electrode for a selection by the device user.

20 Claims, No Drawings

DEVICE FOR PERFORMING tVNS TREATMENT

BACKGROUND OF THE INVENTION

The present invention relates to a device for performing a tVNS treatment in accordance with the description herein.

So-called transcutaneous vagus nerve stimulation (also called tVNS in the following) is known from the prior art as a treatment method that is based on a branch of the vagus nerve, namely the Ramus auricularis nervi vagi (RANV), being transcutaneously stimulated by electrical pulses. The method is used, for example, in the treatment of medically refractive epilepsy (MRE) and refractive depression.

The treatment is carried out with a device that generates electrical pulses that are delivered through the skin to said branch of the vagus nerve by an ear electrode that is worn like an earphone.

It is known from the prior art that the process of tVNS runs in accordance with a fixed stimulation protocol.

The device works through this stimulation protocol, that is stored in a memory, with fixed parameters after the switching on.

This procedure is inflexible to the extent that no optimization of the treatment is possible with respect to the wellbeing of the patient.

SUMMARY OF THE INVENTION

It is therefore the underlying object of the invention to further develop a device of the initially named kind such that it enables an optimization of the treatment with respect to conventional devices.

This object is achieved by a device having the features herein.

Provision is accordingly made that the device for performing a tVNS treatment is configured with at least one electrode for generating a stimulation pulse, wherein the device has at least one input device for inputting feedback data by the device user, wherein the device has a memory in which the feedback data are stored, and wherein the device has a control or regulation unit that is suitable to set one or more parameters of the stimulation pulse delivered by the electrode in dependence on the feedback data or to propose the parameters of the stimulation pulse delivered by the electrode for a selection by the device user, e.g. by display on a screen.

Instead of a few subjects as part of a defined study, in accordance with the invention, the effect of the device is optimized by feedback of the users while taking account of defined parameters.

The device knows the defined parameters of the pulse delivered by the electrode and learns by the feedback of the user or users whether these parameters have resulted in complaints such as headaches, etc. or whether an abatement or worsening has occurred or whether the wellbeing of the patient has improved or worsened.

Based on this feedback, the device can change the stimulation pulse on the next treatment or treatments such that ultimately a positive change occurs in the patient, i.e. an optimization is performed solely or inter alia on the basis of the feedback data.

The technical settings of the device such as the pulse duration, length, intensity, etc. are set in dependence on the feedback of the device user or users or are proposed for setting by the user so that he can decide himself whether he would like to follow the proposal.

Said optimization is possible for a large number of device users so that a very large amount of data can be obtained that allows a more targeted optimization of the parameter or parameters of the pulses delivered by the electrode.

The parameter or parameters of the stimulation pulse delivered by the electrode can represent its duration, strength, or frequency, or a combination of these parameters. Other possible parameters of the stimulation pulse can also be set in dependence on the feedback data or can be proposed.

It is conceivable that the feedback data stored in the memory are individual to the patient. This means that an optimization of the stimulation pulse individual to the patient is carried out.

It is also conceivable and covered by the invention that the feedback data stored in the memory are not individual to the patient, but rather relate to all the device users or to a majority of device users.

In this case, no setting of the stimulation pulse individual to the patient takes place, but the feedback data of a majority of users are rather detected and an optimization of the stimulation pulse is then carried out in dependence thereon for all device users or for a majority of device users.

The memory in which the feedback data are stored can be an integral component of the device or can be arranged as an external device component. This also applies in another respect to all the other components of the device.

In other words, the term "device" is not only to be understood as a compact device, but also as a system of components that do not necessarily have to be arranged at one and the same location. The memory can thus, for example, be formed as a data pool by a server that is spatially separate from that part of the device the user actuates.

It is conceivable that only a 2-point communication link from the input means to the memory is present.

It can be expanded by the inclusion of third parties such as physicians or psychologists and/or to other device users. These third parties are then able to provide additional advice how the treatment by the tVNS device can be further optimized.

The device can comprise means for delivering acoustic stimuli such as music or relaxation instructions to the device user.

Provision is preferably made here that the means have a communication link to the memory and the acoustic stimuli are stored in the memory, with the control or regulation unit being suitable to also set the one or more parameters of the stimulation pulse delivered by the electrode in dependence on the acoustic stimulus or stimuli or to propose these parameters for a selection by the device user.

The device is preferably portable and can in particular be held in the hand. It preferably has the size of a smartphone.

The kind of input device is as desired. A particularly simple design results if the input device is or comprises a touchscreen.

The device can have one or more sensors by means of which one or more patient parameters and/or external parameters can be detected, with the control or regulation unit being configured also to set one or more parameters of the stimulation pulse delivered by the electrode in dependence on the patient parameters and/or on the external parameters or to propose the parameters of the stimulation pulse delivered by the electrode for a selection by the device user.

In this case, these parameters such as the heart rate, weather conditions, etc. also enter into the parameter values of the stimulation pulse.

The electrode or electrodes are preferably an ear electrode.

Provision can be made in accordance with a method for the device for performing a tVNS treatment that feedback data that are stored in a memory are input by the device user by means of an input device and that one or more parameters of the stimulation pulse delivered by the electrode are set in in dependence on the feedback data or are proposed for a selection by the user.

DESCRIPTION OF THE PREFERRED EMBODIMENTS

Preferred features of the method can be found in the description herein.

It is pointed out at this point that the terms "a" and "one" do not necessarily refer to exactly one of the elements, even though this represents a possible embodiment, but can also designate a plurality of elements. The use of the plural equally also includes the presence of the element in question in the singular and, conversely, the singular also includes a plurality of the elements in question.

Further details and advantages of the invention will be explained in more detail with reference to an embodiment described in the following.

The perceived wellbeing of the user can be increased by the tVNS device in accordance with the invention or a perceptible improvement of a state experienced as negative can be achieved.

"Medical conditions" such as tinnitus, headache, depressive moods, obesity, etc. are meant by way of example as negatively experienced states.

Provision is made to achieve this perceptible improvement that the user provides feedback on his wellbeing during or after the treatment. These feedback data are stored and are used in a following treatment to optimize the parameter values of the delivered pulse such that the wellbeing of the patient is improved in the next treatment. This can be achieved, for example, in that the intensity or duration of the stimulation pulse is changed.

Further factors influencing the parameter values of the stimulation pulse can be external parameters such as the weather or the time of day; on the other hand individual variables such as age, sex, but also preceding activities, perceived tiredness, perceived stress, etc.

Provision is preferably made to collect as many of these variables as possible in a first step. In addition, the technical settings have to be varied and correspondingly collected in a reproducible manner.

All these collected data and the feedback data form a large data pool. This data pool has to be analyzed—in particular for positive and negative links between the variables with respect to their effects on the perceived wellbeing or the perceived change of a negative state.

As a result, recommended actions are formed for the individual user, optionally also for whole user groups. These recommended actions are continuously optimized on the basis of the data present.

Studies of the previously customary kind can be dispensed with using this procedure. The outlined data pool-oriented procedure is rather superior due to the individual tailoring of the results and the continuous optimization of the results.

Any uncertainty that may be present in the collection of the data on the user's own perception and on the further factors is more than compensated by the amount and constant updating of the data.

Conceivable applications of the method or of the tVNS device in accordance with the invention are e.g.
- tinnitus
- quitting smoking
- headache/light migraines
- falls in concentration
- being overweight
- mild dementia
- depressive moods
- stress reduction
- eating disorders
- high blood pressure.

All these parameters or also individual ones of them can be perceived by the patient and reported back to the device as feedback.

The control or regulation unit can generally be configured to carry out an optimization directly for a specific parameter such as headaches, or, in the ideal case, to carry out the optimization such that the symptoms of the patient improve overall.

The invention claimed is:

1. A device for performing a transcutaneous vagus nerve stimulation treatment having at least one electrode for generating a stimulation pulse, wherein
   the device has at least one input device for inputting feedback data by device users, wherein the feedback data includes a user's personal perception and data based on further factors;
   the device has a memory in which the feedback data are stored;
   the device has a control or regulation unit that is suitable to set one or more parameters of the stimulation pulse delivered by the electrode in dependence on the feedback data or to propose the parameters of the stimulation pulse delivered by the electrode for selection by a device user who is a patient;
   the electrode is arranged to deliver the one or more parameters of the stimulation pulse representing its duration, strength, or frequency, or a combination of these parameters;
   the control or regulation unit is operable to set one or more parameters of the stimulation pulse delivered by the electrode in dependence on the stored feedback data;
   the control or regulation unit is operable to activate a targeted optimization of the one or more parameters of the stimulation pulse based on solely or inter alia the feedback data stored in the memory to improve a next treatment; and
   the memory stores feedback data not individual to the patient, but rather related to all other device users or to a majority of said device users;
   based on the feedback data, the device learns whether abatement or worsening has occurred, or wellbeing of the patient has improved or worsened; and
   at least some of the one or more parameters of the stimulation pulse of the other device users are reported back to the device as feedback;
   wherein a data pool is collected with the feedback data from a majority of the other device users, the data pool continuously updated, and wherein the transcutaneous vagus nerve stimulation treatment is performed from the collected data pool of the individual patient or a group of the other device users; and comprising tailoring the data for continuously updating the targeted optimization;

wherein the device has one or more sensors by which one or more patient parameters and external parameters can be detected;

the feedback data as well as the one or more patient parameters and external parameters form the data pool;

the device is configured to analyze variables of the data pool for whether there are positive and negative links between the variables with respect to their effects on the perceived wellbeing and generate an analyzed result, wherein the variables include weather, time of day, age, sex, preceding activity, perceived tiredness, and perceived stress; and the control or regulation unit is suitable to set one or more parameters of the stimulation pulse delivered by the electrode or propose the parameters of the stimulation pulse delivered by the electrode for selection by the device user in dependence on the analyzed result; and wherein the feedback data based on the user's personal perception and the data based on further factors is used in combination with the continuously updated data pool to adjust the stimulation pulse, and wherein the continuously updated data pool is constantly updated.

2. A device in accordance with claim 1, wherein the memory is an integral component of the device or is arranged as an external device component.

3. A device in accordance with claim 1, wherein a 2-point communication link from the input device to the memory is present.

4. A device in accordance with claim 1, wherein a communication link is not only present from the input device to the memory, but there are rather furthermore one or more communication links to external third parties, including physicians or psychologists.

5. A device in accordance with claim 1, wherein the device is configured for delivering acoustic stimuli to the device user.

6. A device in accordance with claim 5, wherein the device has a communication link to the memory and the acoustic stimuli are stored in the memory, with the control or regulation unit being suitable to also set the one or more parameters of the stimulation pulse delivered by the electrode in dependence on the acoustic stimulus or stimuli or to propose these parameters for a selection by the device user.

7. A device in accordance with claim 1, wherein the device is portable and preferably has the size of a smartphone.

8. A device in accordance with claim 1, wherein the input device is or comprises a touchscreen.

9. A device in accordance with claim 1, wherein the parameters of the stimulation pulse are influenced by a detected heart rate or by weather conditions.

10. A device in accordance with claim 1, wherein the electrode is configured to fit on and around an ear of a patient.

11. A device in accordance with claim 1, wherein the control or regulation unit is configured to set one or more parameters of the stimulation pulse to address tinnitus, quitting smoking, headache and light migraines, falls due to lack of concentration, overweight, mild dementia, depressive moods, stress reduction, eating disorders, and high blood pressure.

12. A device in accordance with claim 11, configured so the patient can perceive these parameters and report back to the device as feedback.

13. A device in accordance with claim 1, wherein as many of the variables are collected in a same, first step to form the variables of the data pool that are analyzed for whether there are the positive and negative links.

14. A device in accordance with claim 4, wherein the external third parties further include other device users.

15. A device in accordance with claim 1, wherein the analyzed variables of the data pool compensate for uncertainty present in the user's personal perception.

16. A device in accordance with claim 1, wherein the variables further include multiple different medical conditions, and wherein the multiple different medical conditions include tinnitus.

17. A device in accordance with claim 1, wherein the variables further include multiple different medical conditions, and wherein the multiple different medical conditions include headache.

18. A device in accordance with claim 1, wherein the variables further include multiple different medical conditions, and wherein the multiple different medical conditions include depressive moods.

19. A device in accordance with claim 1, wherein the variables further include multiple different medical conditions, and wherein the multiple different medical conditions include obesity.

20. A device in accordance with claim 1, wherein the variables further include multiple different medical conditions, and wherein the multiple different medical conditions are each negatively experienced states for the device users.

* * * * *